(12) United States Patent
Zinger et al.

(10) Patent No.: US 6,558,365 B2
(45) Date of Patent: May 6, 2003

(54) FLUID TRANSFER DEVICE

(75) Inventors: Freddy Zinger, Ra'anana (IL); Igor Denenburg, Rehovt (IL)

(73) Assignee: Medimop Medical Projects, Ltd.

( * ) Notice: Subject to any disclaimer, the term of this patent is extended or adjusted under 35 U.S.C. 154(b) by 38 days.

(21) Appl. No.: 09/754,709

(22) Filed: Jan. 3, 2001

(65) Prior Publication Data

US 2002/0087141 A1 Jul. 4, 2002

(51) Int. Cl.[7] .............................................. A61B 19/00
(52) U.S. Cl. ...................... 604/410; 604/411; 604/412; 604/413; 604/414; 604/415; 141/329; 141/330; 141/383; 141/386
(58) Field of Search ................................ 604/410, 411, 604/412, 414, 416, 415, 413; 141/329, 330, 320, 383, 386

(56) References Cited

U.S. PATENT DOCUMENTS

| | | | |
|---|---|---|---|
| 3,484,849 A | * 12/1969 | Huebner et al. ............ 137/575 |
| 4,614,437 A | * 9/1986 | Buehler ...................... 366/130 |
| 4,638,975 A | 1/1987 | Iuchi et al. |
| 4,639,019 A | * 1/1987 | Mittleman .................. 285/352 |
| 4,743,229 A | * 5/1988 | Chu ............................ 604/82 |
| 4,997,430 A | 3/1991 | VanderHeiden et al. |
| 5,049,129 A | * 9/1991 | Zdeb et al. ................... 604/85 |
| 5,104,387 A | 4/1992 | Pokorney et al. |
| 5,334,163 A | 8/1994 | Sinnett |
| 5,342,346 A | * 8/1994 | Honda et al. ................ 604/413 |
| 5,350,372 A | * 9/1994 | Ideda et al. .................. 606/414 |
| 5,385,547 A | * 1/1995 | Wong et al. ................... 604/87 |
| 5,478,337 A | * 12/1995 | Okamoto et al. ............ 604/413 |
| 5,573,281 A | * 11/1996 | Keller .......................... 285/40 |
| 5,636,660 A | * 6/1997 | Pfleiderer et al. ........... 137/550 |
| 5,641,010 A | * 6/1997 | Maier ......................... 141/329 |
| 6,063,068 A | * 5/2000 | Fowles et al. ............... 604/414 |
| D427,308 S | * 6/2000 | Zinger ....................... D24/129 |
| 6,080,132 A | * 6/2000 | Cole et al. .................... 604/85 |
| 6,156,025 A | * 12/2000 | Niedospial, Jr. et al. .... 604/408 |

* cited by examiner

Primary Examiner—Ira S. Lazarus
Assistant Examiner—Tu Cam Nguyen
(74) Attorney, Agent, or Firm—James E. Brunton

(57) ABSTRACT

A fluid transfer and mixing device for use in the aseptic intermixing of a powder component with a fluid component. The device is of a simple, compact construction that includes a first adapter that can be easily connected to a container containing the powder component and a second adapter that can be removably interconnected with the first adapter and can also be readily connected to a container containing a fluid such as a diluent so as to permit aseptic intermixing of the diluent with the powder. In use a conventional needleless syringe can be easily connected to the first adapter so that the mixture of the powder and diluent can be aseptically aspirated from the first container for subsequent delivery to the patient.

13 Claims, 7 Drawing Sheets

FLUID TRANSFER DEVICE

BACKGROUND OF THE INVENTION

1. Field of the Invention

The present invention relates generally to transfer devices for use in mixing medicinal substances. More particularly, the invention concerns a novel fluid transfer and mixing device for intermixing a fluid with a powdered medicament and for the aseptic delivery of the mixture to a patient.

2. Discussion of the Invention

Many medicinal agents intended for parenteral administration are stored in powder form in a bottle or vial under vacuum. The dry medicinal agent in powdered form typically requires reconstitution with a suitable diluent prior to administration. In the past, the diluent has been provided either in a pre-filled syringe or in a glass vial or bottle. The vial or bottle is generally closed by an elastomeric stopper which can be penetrated by a piercing member as, for example, sharp end or blunt end needle. The elastomeric stopper, which may be slit to accept a blunt end cannula, is typically self-closing upon withdrawal of the piercing member. As previously mentioned, when the drug or other beneficial agent is in powdered or lyophilized form, the vial or bottle is under a relatively high vacuum.

In the past, the medicament to be delivered to the patient has been prepared by filling a conventional syringe with an appropriate diluent. The seal of the container containing the powder is then pierced by the needle of the filled syringe and the diluent is injected into the container to intermix with the powder. The mixture thus formed is then allowed to aspirate back into the syringe so that it can be delivered to the patient in a conventional manner.

Drawbacks of this type of prior art method include the possibility of highly undesirable needlestick. Additionally, the prior art method is troublesome because of the difficulty of locating the center of the stopper or seal of the container that is to be pierced. Further, considerable skill and experience is required to withdraw the entire contents of the medicament from the container containing the mixture of the powder and the diluent so that a proper dose can be delivered to the patient.

It is vitally important that the intermixing of the diluent and the powdered agent be done under sterile conditions. Similarly, the transfer of the reconstituted medicinal agent from the vial or bottle into a suitable administration means, such as a syringe, must be done in a careful and sterile manner. The problem of ensuring such fluid transfers under aseptic conditions is especially acute in the case of self-administration of drugs by patients in a home-care environment.

A useful apparatus for accomplishing the sterile intermixing and subsequent delivery of the reconstituted beneficial agent to a patient is described in copending U.S. Ser. No. 08/913,432 filed by the present inventor. This application is hereby incorporated by reference as though fully set forth herein. One embodiment of the invention described in the incorporated-by-reference application comprises a fluid control device for the preparation of a medicament by mixing a first substance contained within a first medicinal vessel with a second substance contained in a second medicinal vessel and thereafter the transferring of the drug to a dispensing tool, namely, a syringe. A principal feature of the fluid control device of this earlier-filed application resides in the provision of a base member having a generally tubular intermediate portion defining a lumen in which a flow control member is rotatably inserted. The flow control member has a port fashioned as a female luer connector for receiving a dispensing tool such as a syringe. The flow control member includes integrally formed handles for enabling the manual rotation thereof.

As will be better understood from the description that follows, the apparatus of the present invention uniquely eliminates the flow control member found in the apparatus described in the previously filed application thereby simplifying the construction of the device and making it much easier to use and considerably less costly to manufacture. More particularly, the apparatus of the present invention uniquely comprises a greatly simplified, two component mixing device that includes first and second cooperating adapters of novel design. The first adapter, which is used to access a first container, includes a top wall, a cannula depending from the top wall and a resiliently deformable skirt connected to the top wall for telescopically receiving the upper portion of the first container that contains a powdered medicament. The second adapter of the apparatus, which is used for accessing a second container, can be readily connected to and disconnected from the first adapter. In one form of the invention, the second adapter, like the first adapter comprises a top wall, a cannula depending from the top wall and a resiliently deformable skirt connected to said top wall for telescopically receiving the upper portion of the second container that contains a diluent.

In using the apparatus of one form of the present invention, the first and second adapters are first interconnected and the assemblage thus formed is then connected to the first container containing the lyophilized or powdered medicament. Next the second, or diluent container is connected to the adapter assemblage so that the diluent can flow through the assemblage and directly into the first container where it will intermix with the powder contained therewithin. This done, the second adapter along with the diluent container is disconnected from the first adapter. With the first adapter still connected to the first container, which now contains the reconstituted medicament that is to be administered to the patient, the second container is accessed by a needleless syringe so that the mixture can be aspirated from the second container and delivered to the patient in a conventional manner using the thusly filled syringe.

Other prior art fluid control and coupler devices known to applicant include U.S. Pat. No. 4,638,975 issued to Iuchi et al; U.S. Pat. No. 4,997,420 issued to Van Der Heiden et al; U.S. Pat. No. 5,104,387 issued to Pokorney et al; and U.S. Pat. No. 5,334,163 issued to Sinnett.

SUMMARY OF THE INVENTION

It is an object of the present invention to provide a novel, easy-to-use fluid transfer and mixing device for use in the aseptic intermixing of a powder component with a fluid component.

Another object of the invention is to provide a device of the aforementioned character that is of a simple, compact construction that includes a first adapter that can be easily connected to a container containing the powder component and a second adapter that can be removably interconnected with the first adapter and can also be readily connected to a container containing a fluid such as a diluent so as to permit aseptic intermixing of the diluent with the powder.

Another object of the invention is to provide a device as described in the preceding paragraph in which a conventional needleless syringe can be easily connected to the first adapter so that the mixture of powder and diluent can be aseptically aspirated from the first container for subsequent delivery to the patient.

Another object of the invention is to provide a transfer and mixing device that includes filter means for filtering particulate matter from the mixture to be delivered to the patient.

Another object of the invention is to provide a device of the character described which both avoids needlestick and at the same time is very easy to use because the first and second adapters are designed to effortlessly and precisely snap onto and securely grip the first and second containers.

Another object of the invention is to provide a device that is uniquely designed so that, after the mixing step and upon separation of the first and second adapters by relative rotation thereof, the user is left with an adapter that is already connected to the container containing the medicament mixture to be delivered and has ready access to a luer connector provided on the adapter to which a needleless syringe can be easily connected.

Another object of the invention is to provide a device as described in the preceding paragraph that includes valving means for controlling fluid flow through the first adapter.

Another object of the invention is to provide a third transfer apparatus of the class described which is of a simple construction, can readily be used in the home care environment and one that can be inexpensively manufactured in quantity.

These and other objects of the invention are satisfied by the apparatus of the invention that will be described in the paragraphs that follow.

DESCRIPTION OF THE INVENTION

Figure 1:
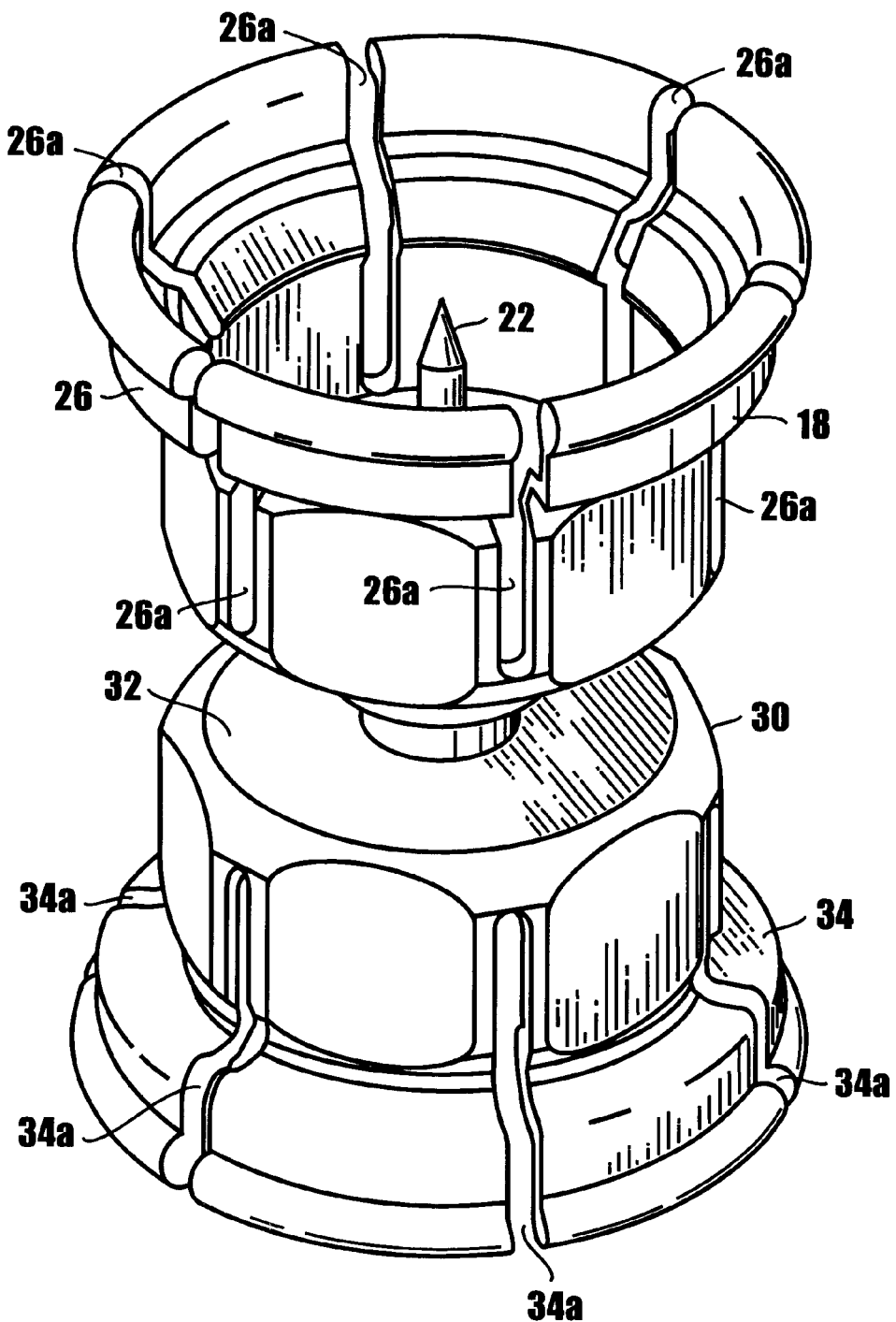
FIG. 1 is a generally perspective view of the first and second adapters of the invention shown in an interconnected configuration.
Figure 2:
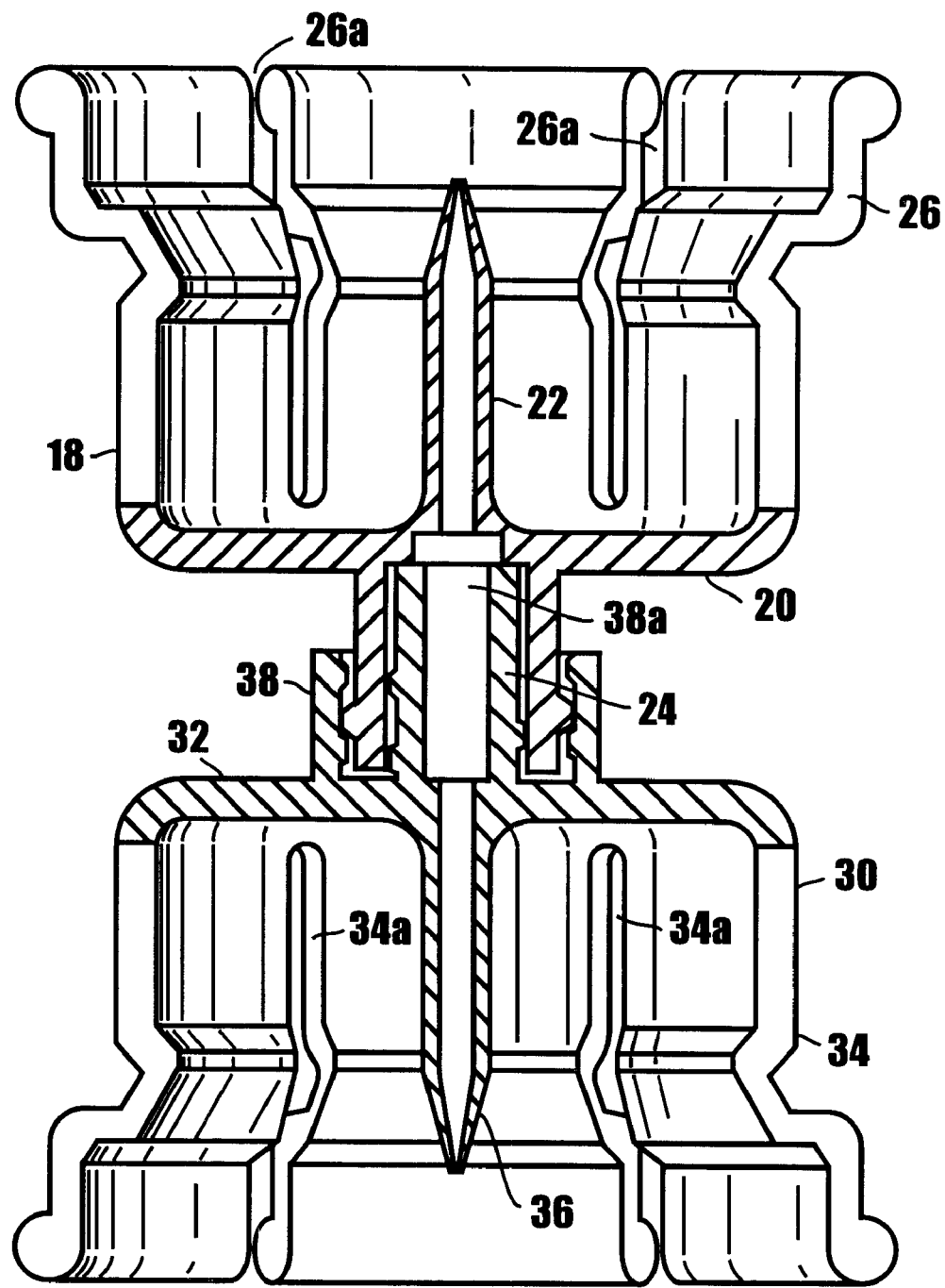
FIG. 2 is a view partly in cross section of the assemblage shown in FIG. 1.
Figure 3:
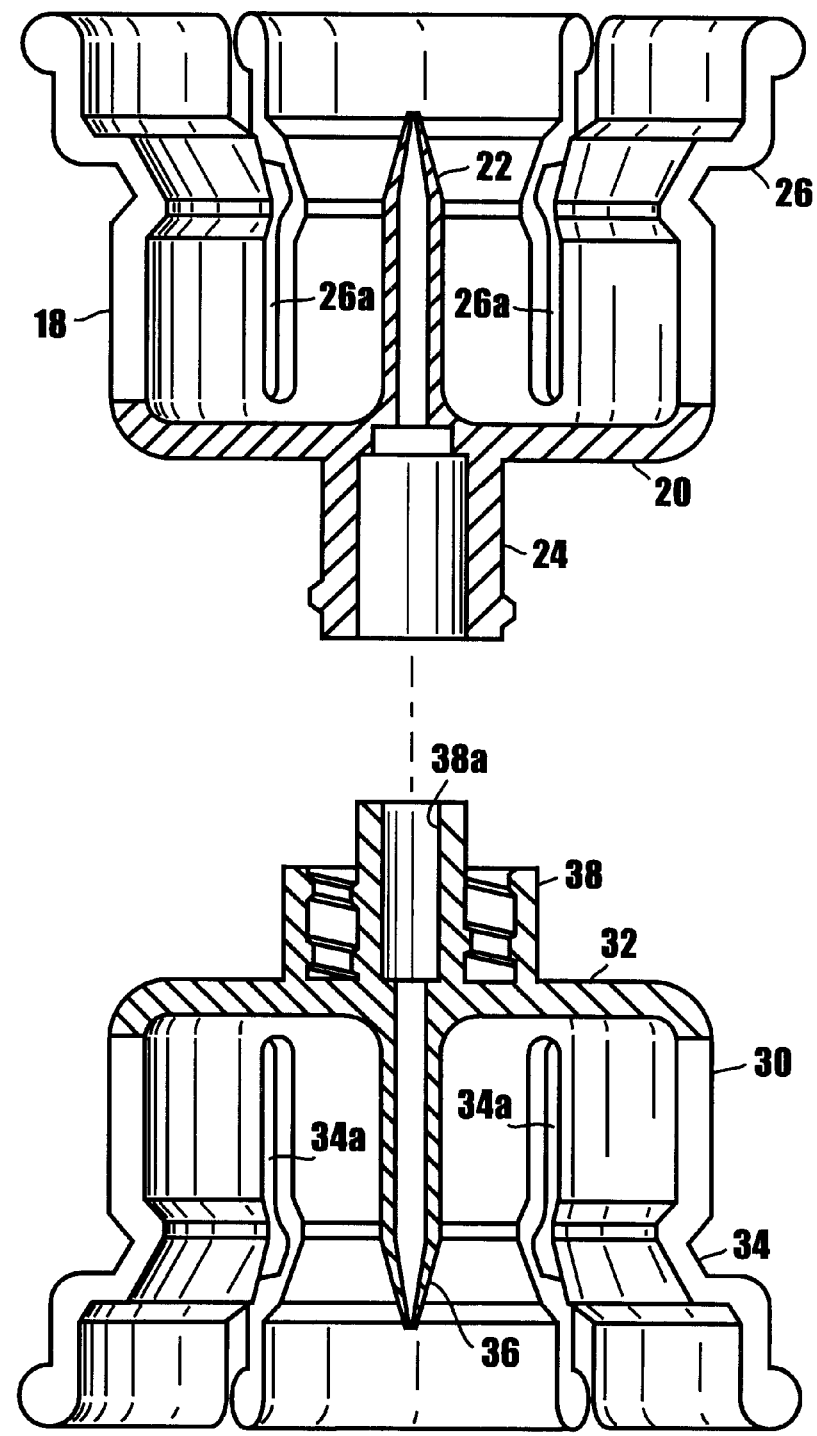
FIG. 3 is an exploded view of the assemblage shown in FIG. 2.
Figure 5:
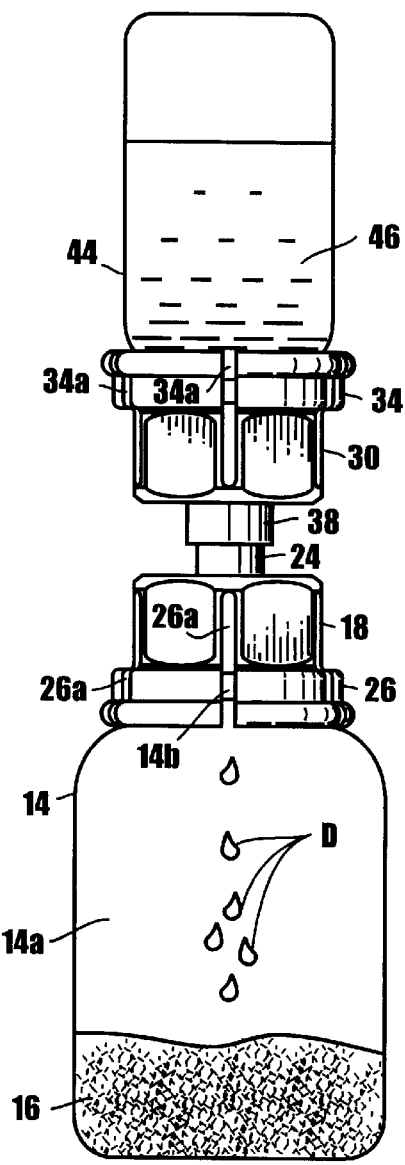
FIG. 5 is a side-elevational view showing the assemblage of FIG. 4 interconnected with a container containing a powdered medicament.

Referring to the drawings and particularly to FIGS. 1, 2 and 3, one form of the apparatus of the invention for transferring and mixing first and second substances contained within first and second containers to form a mixture that can be delivered to a patient is there illustrated. As shown in FIG. 5, the first container 14 includes a container portion 14a that contains a powered or lypholized substance 16. Container 14 also includes an upper, generally cylindrically shaped portion 14b over which the first adapter 18 of the apparatus is closely received (see also FIG. 2).

Adapter 18 is uniquely designed to gain access to container portion 14a of container 14 via a piercing cannula and here includes a top wall 20. Extending from top wall 20 is the hollow, piercing cannula 22 that protrudes into a resiliently deformable, umbrella-like skirt, the construction of which will presently be described. Also extending from top wall 20 in an opposite direction is first connector 24 (see also FIG. 3). Container 14 is of conventional construction and includes an elastomeric seal or stopper (not shown) that seals the open upper end of the generally cylindrically shaped portion 14b. Accordingly, when first adapter 18 is mated with container 14, in the manner shown in FIG. 4, hollow cannula 22 will pierce the elastomeric stopper opening communication between container portion 14a and connector 24.

As best seen in FIGS. 2 and 3, adapter 18 also includes the previously mentioned, resiliently deformable skirt 26 that is connected to top wall 20. Skirt 26 here comprises the first connector means of the invention for interconnecting the first adapter with the first container. Skirt portion 26 is provided with a plurality of circumferentially spaced slits 26a that permit the skirt to securely snap over upper portion 14b of container 14 and into the configuration shown in FIG. 5 of the drawings.

Figure 7:
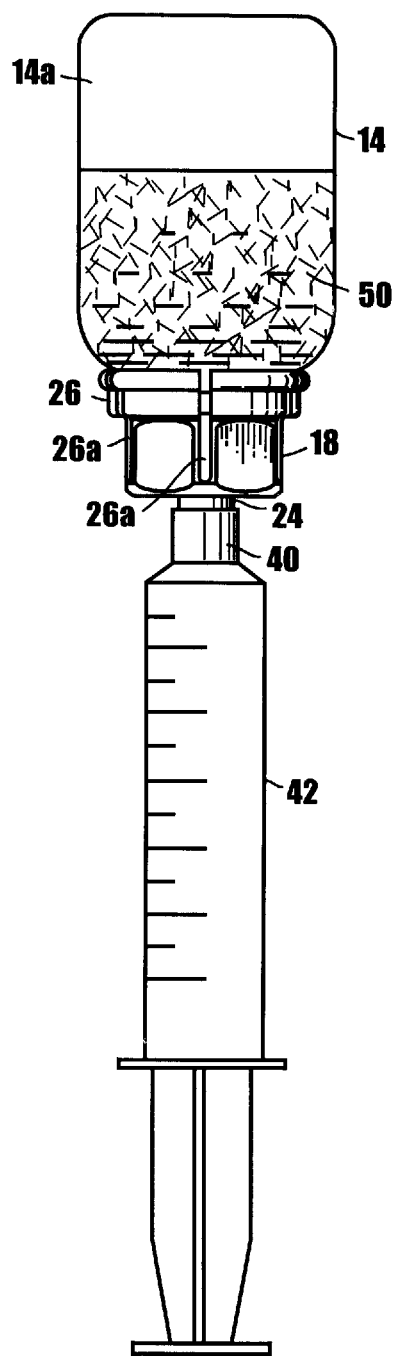
FIG. 7 is a side-elevational view showing the assemblage of FIG. 6 interconnected with a conventional needleless syringe assembly.
Figure 8:
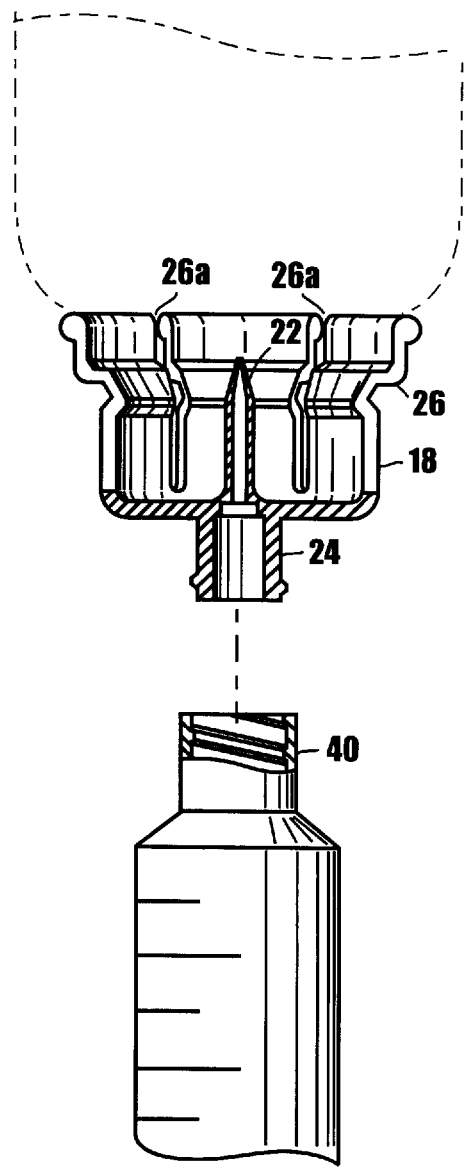
FIG. 8 is an enlarged fragmentary side-elevational view similar to FIG. 7, but showing the syringe assembly separated from the first adapter.

Threadably connected to the first adapter 18 is a second adapter 30 which is of the configuration best seen in FIGS. 2 and 3. Second container 30 also includes a top wall 32 and a resiliently deformable skirt portion 34 that is connected to top wall 32. Skirt portion 34, which comprises the second connector means of the invention for interconnecting the second adapter with the second container, also includes a plurality of circumferentially spaced slits 34a. Also connected to top wall 32 and extending therefrom is a second piercing cannula 36 which is of the construction shown in FIGS. 2 and 3. Also connected to and extending from top wall 32 is a second connector 38. While connectors 24 and 38 may take various forms, connector 24 is preferably provided in the form of a male luer connector, while connector 38 is preferably provided in the form of a female luer connector that will mate with connector 24 when the parts are threadably interconnected by relative rotation of the first and second adapters to form the construction shown in FIG. 2. As will be described in greater detail in the paragraphs that follow, connector 24 is also configured to threadably mate with aspirator means having a connector 40 of the type found on conventional, readily commercially available needleless syringes 42 (see FIGS. 7 and 8).

Figure 4:
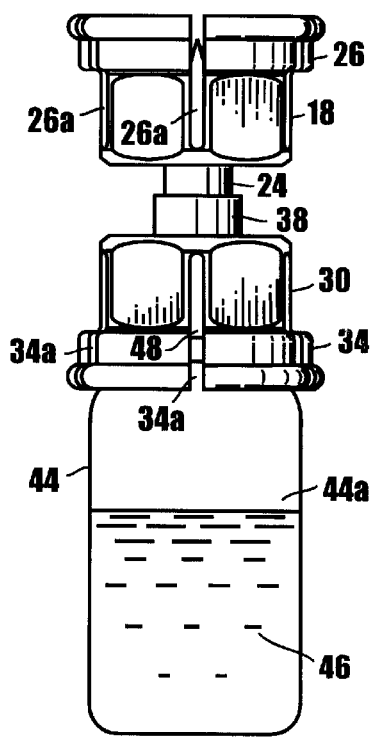
FIG. 4 is a side-elevational view showing the assemblage illustrated in FIG. 1 interconnected with a container containing a fluid.

As shown in FIG. 4, second adapter 30 is adapted to mate with a second container 44. Second container 44 includes a container portion 44a which is here filled with a diluent 46, and an upper, generally cylindrically shaped portion 48 that is also sealably closed by an elastomeric member such as an elastomeric stopper (not shown). Container 44, like container 14, is of conventional construction and is readily commercially available.

With the construction shown in the drawings, second adapter 30 can be mated with container 44 in the manner shown in FIG. 4 with the piercing cannula 36 piercing the elastomeric seal so as to open communication between container portion 44a and the outlet 38a of connector 38.

In using the apparatus of the invention, connector 18 is first threadably interconnected with adapter 30 in the manner shown in FIGS. 1 and 2. The assemblage thus formed is interconnected with container 44 in the manner shown in FIG. 4. This assemblage, which now comprises adapters 18 and 30 and container 44, is next mated with container 14 in the manner shown in FIG. 5. As previously mentioned, container portion 14a is under vacuum so that when hollow cannula 22 pierces the elastomeric seal that seals the upper portion of container 14, the fluid will be automatically and rapidly drawn into container portion 14a in the manner indicated by the droplets "D" in FIG. 5. In a short period of time, the diluent 46 contained within container 44 will flow into container portion 14a of container 14 and will rapidly intermix with the powered or lypholized medicament 16 contained within container 14.

Figure 6:
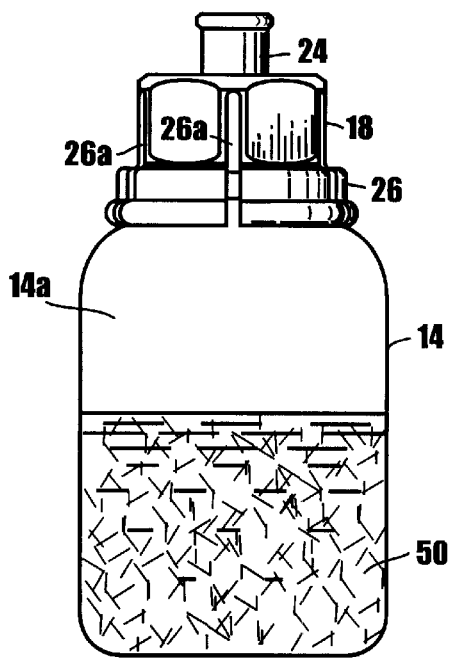
FIG. 6 is a side-elevational view similar to FIG. 5, but showing the assemblage made up of the second adapter and the container that contained the fluid disconnected from the first adapter and a container that originally contained the powered medicine.

Once the diluent and the powered medicament is thoroughly mixed, container 44 along with second adapter 30 is threadably disconnected from adapter 18 to form the configuration shown in FIG. 6 that comprises container 14 and adapter 18. As depicted in FIG. 6, the diluent has now intermixed with the powdered medicament to form the mixture generally designated in FIG. 6 by the numeral 50.

The next step in the method of the invention is to access the assemblage shown in FIG. 6 using the aspirator means which functions to aspirate from container 14 the mixture contained therein. The aspirator means is here provided in the form of a conventional syringe assembly such as syringe assembly 42. This can readily be accomplished by threadably interconnecting connector 40 of the aspirator or syringe assembly with connector 24 of the first adapter 18 so as to form the assemb-lage illustrated in FIG. 7. The aspirator or syringe 42 can then be used in a conventional manner to withdraw the mixture 50 from vial 14 in order to appropriately fill the aspirator or syringe 42. The aspirator can then be disconnected from the assemblage in the manner shown in FIG. 8 so that the mixture 50 that is now contained within the aspirator can be delivered to the patient via an appropriate administration line having a male luer connector affixed thereto.

Figure 9:
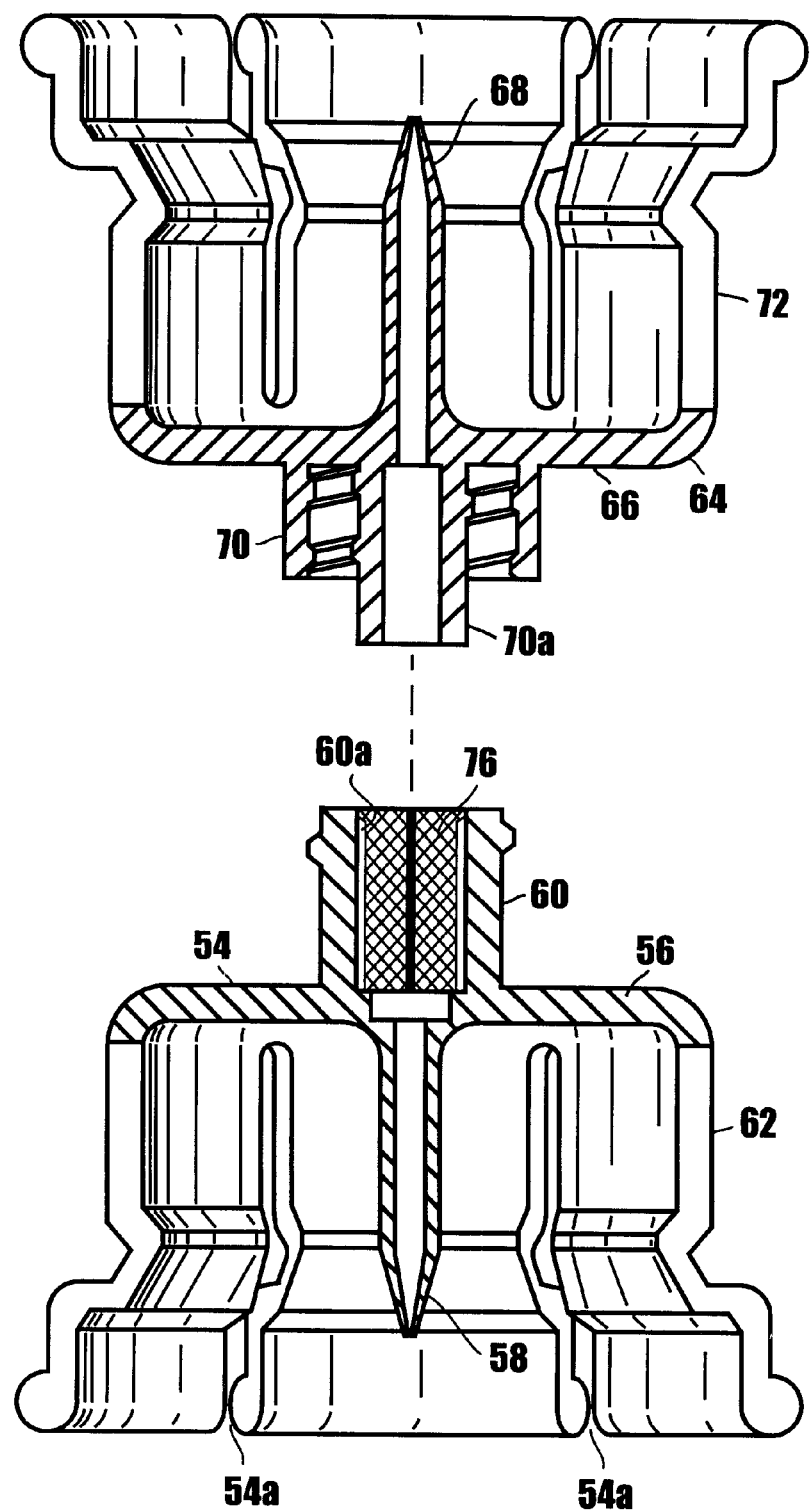
FIG. 9 is a side-elevational view, partly in cross section showing another form of the first and second adapters of the invention shown in an interconnected configuration.
Figure 10:
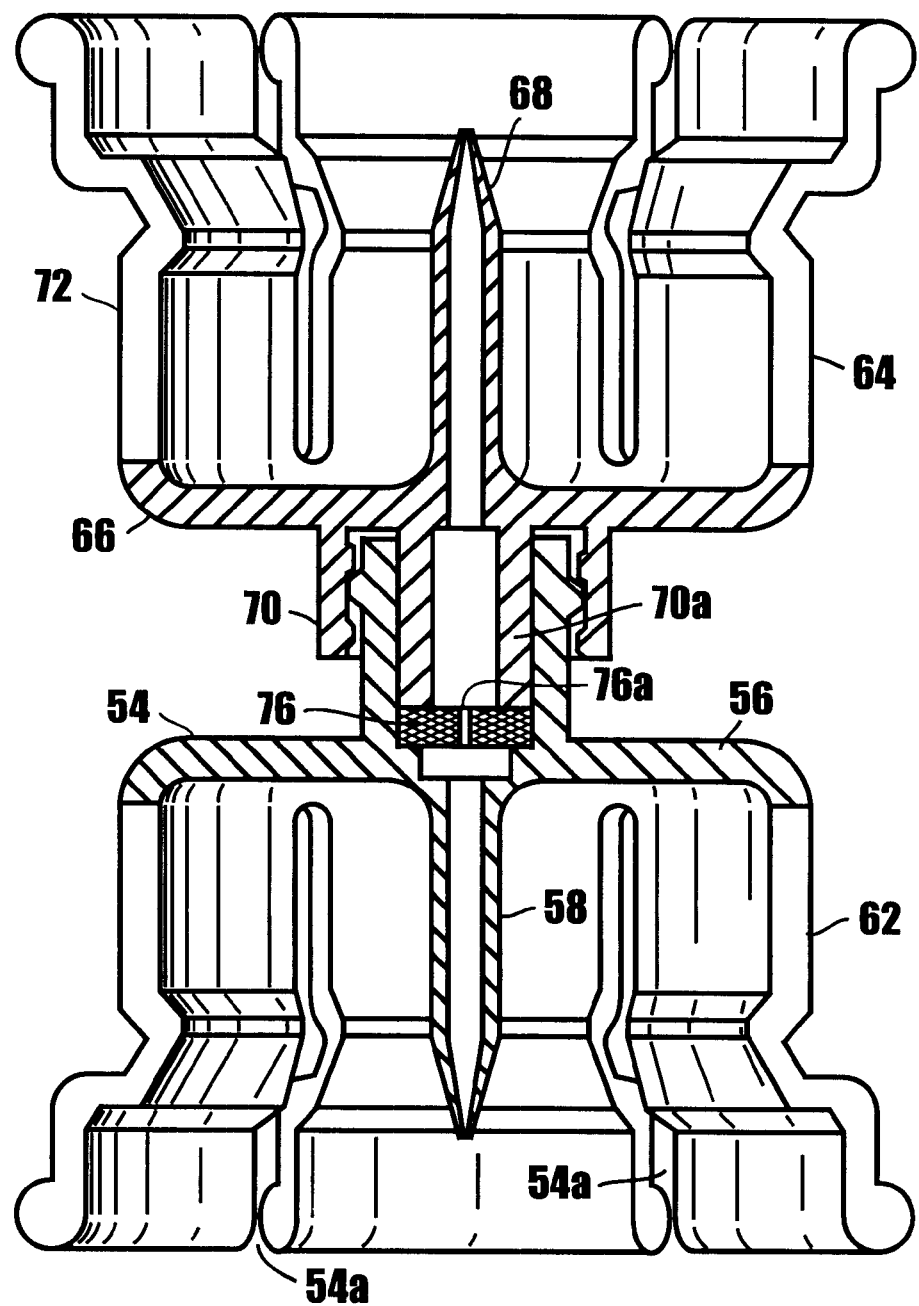
FIG. 10 is a side-elevational view, partly in cross section that is similar to FIG. 9, but showing the valve of the apparatus in an open configuration.

Turning next to FIGS. 9 and 10, an alternate form of the apparatus of the invention is there shown. This apparatus is similar in many respects to that shown in FIGS. 1 through 3 and like numerals are used to identify like components. The primary difference between this latest form of the invention and the earlier described embodiments resides in the fact that valving means is provided within the first adapter to control fluid flow through the connector portion thereof. The character of this novel valving means will presently be described.

First adapter 54 of this latest form of the invention is of similar construction to adapter 18 and includes a top wall 56 from which both a piercing cannula 58 and a connector 60 extend in the manner shown in FIG. 9. Also connected to top wall 56 is a resiliently deformable slitted skirt-like portion 62 which is of similar character to skirt-like portion 26 as previously described.

As before, connector 54 is provided with circumferentially spaced slits 54a and is adapted to be threadably mated with second connector 64 and also with a container, such as container 14, that contains a powered medicament.

Second adapter 64 is of a similar construction to second adapter 30 and includes a top wall 66 from which a piercing cannula 68 and a connector 70 extend in the manner shown in FIG. 9. Also connected to and extending from top wall 66 is a resiliently deformable, slitted skirt-like portion 72 which is of similar construction to skirt-like portion 34 of second adapter 30. As before, second adapter 64 is adapted to be interconnected with a container such as container 44 containing a diluent or other suitable medicinal fluid.

The novel valving means of this latest form of the invention comprises a slitted elastomeric member 76 which is sealably received within the outlet port 60a of connector 60 in the manner illustrated in FIG. 9. Member 76, when in its normal expanded configuration shown in FIG. 9, functions to sealably close outlet 60a. However, when adapter 64 is mated with adapter 62 in the manner shown in FIG. 10, the stem component 70a of connector portion 70 of adapter 64 will function to compress valve member 76 in the manner shown in FIG. 10 thereby opening a fluid flow passageway 76a formed within member 76 so as to permit passage of fluid between the respective connector portions of adapters 62 and 64. With this construction, when adapter 62 is connected to vial 14 (see FIG. 6), the mixture of the diluent and the powdered medicament will be sealably contained within container 14 until the aspirator means, or syringe, 42 is mated with the assemblage in the manner previously discussed. Upon mating the syringe assembly with adapter 54, the valve member 76 will once again be compressed by the stem of the syringe permitting the medicament mixture to be aspirated from the container.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for mixing a first powdered substance contained within a first sealed container under vacuum and a second fluid substance contained within a second sealed container to form a mixture, each said container comprising a container portion and an upper portion, said apparatus comprising:

(a) a first adapter including a top wall, a cannula connected to and extending from said top wall, a first connector connected to and extending from said top wall and a first connector means connected to said top wall for interconnecting said first adapter with the upper portion of the first container;

(b) aspirator means removably interconnected with said first connector of said first adapter for aspirating from the first container the contents thereof; and (c) a second adapter releasably interconnected with said first connector, said second adapter comprising a top wall, a cannula connected to and extending from said top wall and a second connector means connected to said top wall for interconnecting said second adapter with the upper portion of the second container.

2. The apparatus as defined in claim 1 in which each of said first and second connector means includes:

(a) a generally cylindrical body portion; and (b) a marginal container gripping portion connected to said generally cylindrical body portion.

3. The mixing apparatus as defined in claim 1 in which said first adapter further includes filter means for filtering particulate matter from a fluid.

4. The mixing apparatus as defined in claim 1 in which said first adapter further includes valve means for controlling the flow of fluid through said first connector.

5. The mixing apparatus as defined in claim 1 in which said first and second connectors comprise luer connectors.

6. An apparatus for mixing a first lyophilized substance contained within a first sealed container under vacuum and a second liquid substance contained within a second sealed container, each said container comprising a container portion and an upper, generally cylindrically shaped portion, said apparatus comprising:

(a) a first adapter including a top wall, a cannula connected to and extending from said top wall, a first connector connected to and extending from said top wall and a resiliently deformable skirt connected to and extending from said top wall for telescopically receiving the upper portion of the first container;

(b) an aspirator removably interconnected with said first connector; and (c) a second adapter releasably interconnected with said first connector, said second adapter comprising a top wall, a cannula connected to and extending from said top wall and a resiliently deformable skirt connected to and extending from said top wall for telescopically receiving the upper portion of the second container.

7. The mixing apparatus as defined in claim 6 in which each of the said resiliently deformable skirts of said first and second adapters is provided with a plurality of circumferentially spaced slits and each comprises:

(a) a generally cylindrical body portion; and (b) a marginal container gripping portion connected to said generally cylindrical body portion.

8. The mixing apparatus as defined in claim 6 in which said first and second connectors comprise luer connectors.

9. A mixing apparatus for mixing a powder contained within a first sealed container under vacuum and a fluid contained within a second sealed container, each said first and second container comprising a container portion and an upper, generally cylindrically shaped portion, said apparatus comprising:

(a) a first adapter including a top wall, a first connector connected to the top wall and extending therefrom and a resiliently deformable skirt connected to said top wall and extending therefrom for telescopically receiving the upper portion of the first container, said skirt having a plurality of circumferentially spaced slits formed therein and including:
  (i) a generally cylindrical body portion;
  (ii) a cannula connected to said top wall and extending into said skirt;
  (iii) a marginal container gripping portion; and
  (iv) valve means for controlling the flow of fluid through said first connector;

(b) an aspirator removably connected to said first connector; and (c) a second adapter releasably interconnected with said first adapter, said second adapter comprising a top wall and a resiliently deformable skirt connected to said top wall and extending therefrom for telescopically receiving the upper portion of the second container, said skirt having a plurality of circumferentially spaced slits formed therein and including:
  (i) a generally cylindrical body portion;
  (ii) a cannula connected to said top wall and extending into said skirt; and
  (iii) a marginal container gripping portion.

10. The mixing apparatus as defined in claim 9 in which said first adapter further includes filter means disposed within said first connector for filtering particulate matter from a fluid.

11. The mixing apparatus as defined in claim 9 in which said first and second adapters are threadably interconnected.

12. The mixing apparatus as defined in claim 9 in which said aspirator comprises a syringe threadably connected to said first connector of said first adapter.

13. The mixing apparatus as defined in claim 9 in which said first and second connectors comprise luer connectors.

* * * * *